United States Patent [19]

Haeberle et al.

[11] Patent Number: 5,221,759
[45] Date of Patent: Jun. 22, 1993

[54] CYCLOSILOXANES CONTAINING MESOGENIC SIDE GROUPS

[75] Inventors: Norman Haeberle, Munich; Wolfgang Haas, Germering; Franz-Heinrich Kreuzer, Martinsried, all of Fed. Rep. of Germany

[73] Assignee: Consortium für elektrochemische Industried GmbH, Munich, Fed. Rep. of Germany

[21] Appl. No.: 728,479

[22] Filed: Jul. 11, 1991

[30] Foreign Application Priority Data

Jul. 12, 1990 [DE] Fed. Rep. of Germany ....... 4022151

[51] Int. Cl.$^5$ .......................... C07F 7/04; C07F 7/10; C07F 7/08; C07F 7/21
[52] U.S. Cl. .................................. 556/413; 556/415; 556/422; 556/425; 556/434; 556/438; 556/451; 556/460; 556/461
[58] Field of Search ............... 556/413, 422, 425, 438, 556/451, 434, 460, 461, 415

[56] References Cited

U.S. PATENT DOCUMENTS

| | | | |
|---|---|---|---|
| 3,560,435 | 2/1971 | Lee et al. | 556/434 |
| 4,410,570 | 10/1983 | Kreuzer et al. | 427/374.1 |
| 4,902,731 | 2/1990 | Leibfried | 556/434 |
| 4,914,221 | 4/1990 | Winkler et al. | 556/436 |

FOREIGN PATENT DOCUMENTS

0431466 6/1991 European Pat. Off. .

OTHER PUBLICATIONS

Journal of the Chemical Society, Chemical Communications, Nr. 2, Jan. 15, 1990, S. 95-97, "Liquid crystalline cyclic polymers".

Chemical Abstracts, Bank 97, 1982, S. 787, Zus.fassung Nr. 2227612c, Columbus, Ohio, US? JP-A-8256820 (Hitachi Ltd) Apr. 5, 1982.

Chemical Abstracts, Band 102,1985,S.13, Zus.fassung Nr. 149979h, Columbus, Ohio US? & SU-A-1126579 (Institute of Heteroorganic Compounds, Academy of Sciences, U.S.S.R. etc.) Nov. 30, 1984.

Chemical Abstracts, Band 111,1989,S.593,Zus.fassung Nr. 47953p, Columbus, Ohio, US? R. Ortler et al., "Reversible holographic–optical data storage in cholesteric liquid-crystalline siloxanes", & Makromol. Chem., Rapid Commun. 1989,10(4), 189-94.

*Primary Examiner*—José G. Dees
*Assistant Examiner*—Joseph M. Conrad

[57] ABSTRACT

The present invention relates to cyclic siloxanes which have at least one group of formula (1) bonded to a silicon atom $$-(CH_2)_x-R''-[-L-A-]_y-(L)_z-T \qquad (1),$$

in which x is an integer having a value of at least 2, preferably having a value of from 2 to 10, R″ is a chemical bond or a divalent radical of the formula —COO—, —OOC—, —CH$_2$—CH$_2$—, —CH=CH—, —C≡C—, —N=N—, —N=N(O)—, —CH=N—, —N=CH—, —N=N—, —N=N(O)—, —N=CH—, —CH=N—, or —Si(R)$_2$—, where the radical R is identical or different and is an optionally substituted hydrocarbon radical having from 1 to 18 carbon atoms, L which is the same or different represents the 1,4-phenylene or 1,4-cyclohexylene radicals which are optionally 2-, 3-, 5- and/or 6-substituted by at least one radical Q, Q is the same or different radical selected from hydrogen, fluorine or chlorine atoms or cyano, methyl or trifluoromethyl groups, A is the same or different and represents divalent radicals R″ is a chemical bond or a divalent radical of the formula —CH$_2$—O—, or —O—CH$_2$—, y is an integer having a value of from 0 to 10, preferably from 0 to 2, z is an integer having a value of from 0 to 10, preferably from 0 to 2, with the proviso that the sum y+z is at least 1, and T is a cholesteryl radical or a substituted or unsubstituted hydrocarbon radical having from 1 to 18 carbon atoms, in which the substituents are preferably selected from the group consisting of halogen atoms, cyano groups, nitro groups, hydrocarbonoxy groups having from 1 to 10 carbon atoms and mixtures thereof.

5 Claims, No Drawings

CYCLOSILOXANES CONTAINING MESOGENIC SIDE GROUPS

The present invention relates to organocyclosiloxanes containing mesogenic side chains, and more preferably organocyclosiloxanes containing mesogenic side chains which are able to form liquid-crystalline phases.

BACKGROUND OF THE INVENTION

Liquid-crystalline compounds have been disclosed, inter alia, by B. D. Demus, H. Demus and H. Zaschke (Flüssige Kristalle in Tabellen [Liquid Crystals in Tables], 1974; D. Demus and H. Zaschke, Flüssige Kristalle in Tabellen II [Liquid Crystals in Tables II], 1984, VEB-Verlag Leipzig). Mesogenic groups are also described therein, i.e., groups whose presence in a molecule may give the opportunity for the occurrence of liquid-crystalline phases.

Organocyclosiloxanes containing mesogenic side groups are described in U.S. Pat. No. 4,410,570 (published Oct. 18, 1983, F. H. Kreuzer et al., Consortium für elektrochemische Industrie GmbH) in which the liquid-crystalline organocyclosiloxanes have mesogenic groups bonded to the respective silicon atom via a propyleneoxy group. They were prepared by the addition reaction of allyloxy benzoates with a cyclosiloxane containing Si-bonded hydrogen atoms. Siloxanes of this type tend to eliminate propene, forming SiO—C bonds which are hydrolytically unstable.

It is an object of the present invention to provide substances containing mesogenic side groups which have liquid-crystalline properties. Another object of the present invention is to provide substances containing mesogenic side groups having liquid-crystalline properties which can be easily oriented. A further object of the present invention is to provide substances containing mesogenic side groups which have liquid-crystalline properties which are chemically stable.

SUMMARY OF THE INVENTION

The foregoing objects and others which will become apparent from the following description are accomplished in accordance with this invention generally speaking by providing cyclic siloxanes which have at least one group of formula (1) bonded to a silicon atom

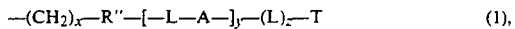

in which x is an integer having a value of at least 2, preferably having a value of from 2 to 10, R" is a chemical bond or a divalent radical of the formula —COO—, —OOC—, —CH$_2$—CH$_2$—, —CH=CH—, —C≡C—, —N=N—, —N=N(O)—, —CH=N—, —N=CH— or —Si(R)$_2$—, where the radical R is the same or different, and is a substituted or unsubstituted hydrocarbon radical having from 1 to 18 carbon atoms, L is the same or different and represents the 1,4-phenylene or 1,4-cyclohexylene radicals which are optionally 2-, 3-, 5- and/or 6-substituted by at least one radical Q, or are 2,5- or 3,6-pyridinediyl, 2,5-pyrimidindiyl, 2,5-pyridazinediyl, 2,5-triazinediyl, 3,6-tetrazinediyl, 2,5-dioxanediyl, 2,5-tetrahydrofurandiyl, 1,3,4-thiadiazole-2,5-diyl or 1,4-bicyclo[2.2.2]octanediyl radicals, Q is the same or different and represents hydrogen, fluorine or chlorine atoms or cyano, methyl or trifluoromethyl groups, A is the same or different and represents divalent radicals R" or radicals of the formula —CH$_2$—O—, and —O—CH$_2$—, y is an integer having a value of from 0 to 10, preferably from 0 to 2, z is an integer having a value of from 0 to 10, preferably from 0 to 2, with the proviso that the sum y+z is at least 1, and T is a cholesteryl radical or a substituted or unsubstituted hydrocarbon radical having from 1 to 18 carbon atoms, in which the substituents are preferably selected from the group consisting of halogen atoms, cyano groups, nitro groups, hydrocarbonoxy groups having from 1 to 10 carbon atoms and mixtures thereof.

DESCRIPTION OF THE INVENTION

The term "at least one group of formula (1) bonded to a silicon atom" means that the group of formula (1) is bonded directly to a silicon atom of the cyclosiloxane.

The radical L is preferably a 1,4-phenylene radical.

Preferred radicals of formula (1) are those of formula (2):

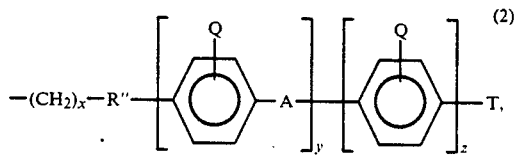

x, y, z, R", Q, A and T are the same as above.

For purposes of the present invention, cyclic siloxanes mean monocyclic cyclosiloxanes, preferably those represented by formula (5):

in which X is the same or different radicals as defined for R or formula (1), with the proviso that q radicals X per molecule are radicals of formula (1), and the radical R" has been replaced in a maximum of q-1 of these radicals of the formula (1) by a radical of the formula —O—, —CH$_2$—O— or —O—CH$_2$—, where q is an integer having a value of from 1 to n and n is an integer having a value of at least 3, and R is the same as above.

Preferably, all the radicals represented by X in formula (5) are radicals of formula (1).

Examples of radicals represented by R are alkyl radicals, such as the methyl, ethyl, n-propyl, isopropyl, n-butyl, isobutyl, tert-butyl, n-pentyl, isopentyl, neopentyl and tert-pentyl radicals, hexyl radicals, such as the n-hexyl radical, heptyl radicals, such as the n-heptyl radical, octyl radicals, such as the n-octyl radical and isooctyl radicals, such as the 2,2,4-trimethylpentyl radical, nonyl radicals, such as the n-nonyl radical, decyl radicals, such as the n-decyl radical, dodecyl radicals, such as the n-dodecyl radical and octadecyl radicals, such as the n-octadecyl radical; cycloalkyl radicals, such as cyclopentyl, cyclohexyl, cycloheptyl and methylcyclohexyl radicals; aryl radicals, such as the phenyl, naphthyl, anthryl and phenanthryl radicals; alkaryl radicals, such as 0-, m- and p-tolyl radicals, xylyl radicals and ethylphenyl radicals; and aralkyl radicals, such as the benzyl radical and the alpha- and β-phenylethyl radicals.

Examples of substituted radicals R are cyanoalkyl radicals, such as the β-cyanoethyl radical, and halogenated hydrocarbon radicals, for example haloalkyl radicals, such as the trifluoromethyl radical and the 3,3,3-trifluoro-n-propyl radical, and haloaryl radicals, such as the o-, m- and p-chlorophenyl radicals.

In the above formulas (1), (2) and (5) and in the formulas below, R is preferably the same or different $C_1$- to $C_8$-alkyl, aryl, aralkyl, alkaryl or cycloalkyl radical and in particular a methyl, ethyl, n-propyl or phenyl radical. At least 80% of the radicals R, and more preferably all the radicals R, are methyl radicals.

In formula (5), all the radicals X are preferably radicals of formula (1), and in particular of formula (2).

In the formulas above and below, x is preferably an integer having a value of from 3 to 12, preferably from 3 to 9, and more preferably from 3 to 6.

The radicals Q are preferably the same or different radicals, namely hydrogen, chlorine or fluorine atoms or cyano radicals, and more preferably hydrogen atoms.

Preferred radicals T are cholesteryl radicals, and radicals of the formulas

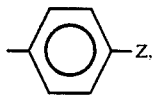 (6)

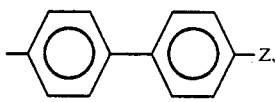 (7)

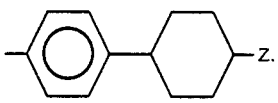 (8)

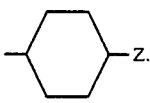 (9)

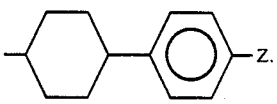 (10)

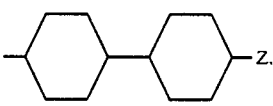 (11)

in which Z is the same or different radicals, namely hydrogen atoms, halogen atoms or cyano, nitro, $C_1$- to $C_6$-alkyl or $C_1$- to $C_6$-alkoxy radicals.

Particularly preferred radicals of formula (1) or (2) and particularly preferred radicals X are those of formula (12):

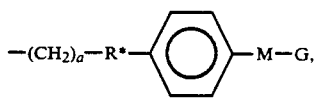 (12)

in which a is the same or different integer having a value of from 2 to 6, R* is the same or different divalent radical, namely a single chemical bond or a radical of the formula —OOC— or —Si(CH$_3$)$_2$—, M is the same or different radical of the formula —OOC—, —COO—, —N=CH— or —CH=N—, and G is a cholesteryl radical or a phenyl or biphenyl radical which is optionally 4-substituted by a halogen atom, a cyano radical, a $C_1$- to $C_4$-alkyl group or an alkoxy group.

Particularly preferred cyclosiloxanes of this invention are organocyclosiloxanes of formula (13):

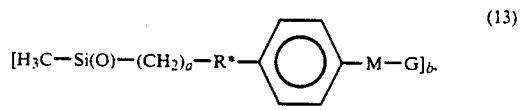 (13)

in which b is an integer having a value of from 3 to 6, and a, R*, M and G are the same as above, with the proviso that, for b-1 radicals of formula (12) in formula (13), the radical R* may also be a radical of the formula —O—.

If the structure permits, the compounds claimed also include the diastereomers and optical isomers thereof, i.e., in particular, the individual enantiomers and mixtures thereof, for example the corresponding racemates.

PROCESSES

Process 1

The cyclosiloxanes of this invention containing mesogenic side groups can be prepared by reacting a cyclic siloxane having at least one hydrogen atom bonded directly to silicon with a compound of formula (14) or (15):

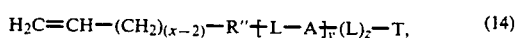 (14)

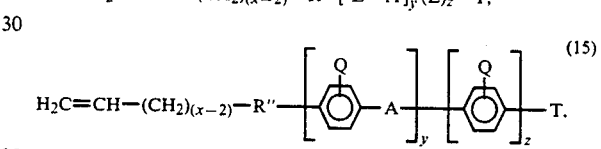 (15)

preferably in the presence of at least one platinum-group metal and/or a compound thereof, where, in the above formulas (14) and (15), R'', L, A, T, x, y, z and Q are the same as above.

The cyclic siloxane having at least one hydrogen atom bonded directly to silicon and employed in the process of this invention is preferably one of the formula

 (19), in which G is identical or different radicals as defined for R or are hydrogen atoms bonded directly to silicon atoms, with the proviso that q radicals X per molecule are hydrogen atoms bonded directly to silicon atoms, q is an integer of from 1 to n and R and n are the same as above for formula (5).

Particularly preferred cyclosiloxanes of formula (19) are those of formula (20):

 (20),

Examples of platinum-group metals and/or of compounds thereof which are referred to as platinum catalysts and are able to accelerate the process according to the invention are platinum, palladium, rhodium, iridium and compounds thereof, preferably platinum and/or compounds thereof. It is possible to employ any catalyst which has been or could have been employed heretofore for the addition reaction of hydrogen atoms bonded directly to Si atoms with aliphatically unsaturated compounds. Examples of catalysts of this type are metallic and finely divided platinum, which may be on a support, such as silica, alumina or activated charcoal, compounds or complexes of platinum, such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum-alkoxide complexes, platinum-ether complexes, platinum-aldehyde complexes, platinum-ketone complexes, including products of the reaction of $H_2PtCl_6 \cdot 6H_2O$ and cyclohexanone, platinum-vinylsiloxane complexes, in particular platinum-divinyltetramethyldisiloxane complexes which contain or are free of detectable inorganically bonded halogen, bis(-gamma-picoline)platinum dichloride, trimethylenedipyridineplatinum dichloride, dicyclopentadieneplatinum dichloride, (dimethyl sulfoxide)ethyleneplatinum(II) dichloride and products of the reaction of platinum tetrachloride with an olefin and a primary amine or secondary amine or a primary and secondary amine, such as the product of the reaction of platinum tetrachloride dissolved in 1-octene with sec-butylamine, or ammonium-platinum complexes as described in EP-B 110 370.

The platinum catalyst is preferably employed in amounts of from 0.02 to 50 mol percent, based on the elemental platinum and based on the number of moles of the particular reaction component, i.e., of the compound(s) of formula (14) or (15) or of the cyclic siloxanes having at least one hydrogen atom bonded directly to silicon, which is present in a substoichiometric amount or in a stoichiometric amount.

The reaction is preferably carried out at temperatures of from 0° C. to 150° C., preferably at pressures of from 0.05 MPa to 2.0 MPa.

If the cyclosiloxane, i.e., preferably that of formula (19) or (20), or the compound of the formula (14) or (15) is very inert, it is also possible to use elevated temperatures, higher pressures and to employ more platinum catalyst.

The reaction is preferably carried out in a solvent, and more preferably an aprotic solvent; solvents or solvent mixtures having a boiling point or boiling range up to about 160° C., preferably up to about 120° C., at 0.1 MPa (abs.). Examples of solvents are esters, such as methyl acetate, ethyl acetate, n- and isopropyl acetate, n-, sec- and t-butyl acetate, ethyl formate and diethyl carbonate; ethers, such as dioxane, tetrahydrofuran, diethyl ether, di-n-propyl ether, diisopropyl ether, di-n-butyl ether, ethylene glycol monomethyl ether, ethylene glycol monoethyl ether, diethylene glycol dimethyl ether and anisole; chlorinated hydrocarbons, such as dichloromethane, trichloromethane, tetrachloromethane, 1,2-dichloroethane, trichloroethylene, tetrachloroethylene and chlorobenzene; hydrocarbons, such as pentane, n-hexane, hexane isomeric mixtures, cyclohexane, heptane, octane, naphtha, petroleum ether, benzene, toluene and xylenes; ketones, such as acetone, methyl ethyl ketone and methyl isobutyl ketone; or mixtures of these solvents.

The term solvent does not mean that all the reaction components must be soluble therein. The reaction can also be carried out in a suspension or emulsion of one or more reactants. The reaction can also be carried out in a solvent mixture having a miscibility gap, at least one reactant being soluble in each of the phases of the mixture.

The cyclic siloxane containing at least one hydrogen atom bonded directly to silicon, preferably a cyclic siloxane of formula (19) or (20), is preferably employed in the process of this invention in a molar ratio, compared to the compound of formula (14) or (15), of from 1:2 to 2:1, in particular from 1:1.1 to 1.1:1.

Preparation of compounds of formula (14) and (15)

Processes for the preparation of starting compounds of the formulas (14) and (15) and of intermediates thereof are described in DE-A 3 935 638. For example, the alkenyl radical can be introduced by reacting the appropriate alkenyl halides with appropriate organometallic benzene derivatives, in particular the Grignard compounds and organolithium compounds. Preferred examples of such benzene derivatives are 4-halobenzenemagnesium halides. The reaction of an alkenyl halide with a benzene derivative is preferably carried out in an inert solvent (mixture), for example diethyl ether, methyl-t-butyl ether, tetrahydrofuran, 1,4-dioxane, hydrocarbons and mixtures thereof, such as benzene, toluene, xylenes, hexane isomer mixtures or petroleum ether. The reaction is preferably carried out at temperatures of from −100° C. to +110° C., in particular at pressures of from 0.09 to 0.11 MPa (abs.). Under certain circumstances, the reaction may be accelerated by ultrasound.

4-(ω-Alkenyl)-1-halobenzenes prepared in this manner can be reacted, inter alia, a second time with magnesium to give the corresponding organomagnesium halides and subsequently with $CO_2$ to give 4-(ω-alkenyl) benzoic acids and finally to give the corresponding cholesteryl or optionally substituted phenyl esters (A=—COO— in formula (14) or (15)). A list of 4-(ω-alkenyl) benozoic acid esters which can be prepared in this manner is given in Table 1.

4-ω-Alkenylphenol derivatives can be obtained by reaction 4-ω-alkenylmagnesium halides with 4-halophenols which are protected on the hydroxyl group, if necessary with a dilithium tetrachlorocuprate catalyst. The phenols obtained in this manner can be esterified using appropriate acids or acid derivatives (A=—OOC— in formula (14) or (15)). Examples of phenol esters which can be prepared correspondingly are given in Table 2.

Reaction of 4-(ω-alkenyl)phenylmagnesium halides (preparable as explained above) with N,N-dimethylformamide gives 4-(ω-alkenyl) benzaldehydes, which in turn react with primary amines, for example with the commercially available 4-alkylanilines, to give the corresponding azomethines (Schiff bases) (A=—CH=N— in formula (14) or (15)). The compound, n-[4-(3-butenylphenyl) benzylidene]-4-butylphenylimine (boiling point at 2 Pa: 170° C.) was prepared in this manner.

Reaction of the 4-(ω-alkenyl)benzaldehydes which can be prepared by the above process with suitable derivatives, for example alkanephosphonic acid esters (Wittig-Horner reaction) give 4-(ω-alkenyl)phenylethylenediyl derivatives (A=—CH=CH— in formula (14) or (15)).

According to EP-A-168 683, Example 26, 1-(ω-alkenyl)-4-nitrobenzene can be reduced to give 4,4'-di(ω-alkenyl)azoxybenzenes, for example by means of magnesium turnings in methanol as solvent (A=—N=N(O)— in formula (14) or (15)). This compound can in turn be reduced in a known manner to give the corresponding azobenzene (A=—N=N— in formula (14) or (15)), for example by means of zinc and sodium hydroxide solution.

All the processes for preparing these and other compounds of formulas (14) and (15) and for the starting materials under process 2 are known and are described, for example, in Houben-Weyl, Methoden der organischen Chemie [Methods of Organic Chemistry], Georg Thieme Verlag, Stuttgart and New York.

Some of the cyclic siloxanes which have at least one hydrogen atom bonded directly to silicon and are employed in process 1 are commercially available from Petrarch Systems (represented by ABCR GmbH & Co. KG, D-7500 Karlsruhe). Their preparation is described, inter alia, in U.S. Pat. No. 2,389.806 and by R. O. Sauer et al. (Journal of the American Chemical Society 68, 962 (1946)). A review of siloxanes and their preparation is given by W. Noll in "Chemistry and Technology of Silicones", Academic Press Inc., Orlando, 1968.

Process 2

The cyclosiloxanes of this invention containing mesogenic side groups can be prepared by reacting a cyclic siloxane containing at least one alkenyl group of the formula

$$-(CH_2)_{(x-2)}-CH=CH_2 \qquad (16),$$

which is bonded directly to silicon with a compound of formula (17) or (18)

$$H-R''+L-A+_y(L)_z-T, \qquad (17)$$

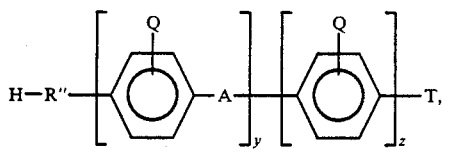

(18)

preferably in the presence of at least one platinum-group metal and/or compounds thereof, where, in the above formulas (16), (17) and (18), L, A, T, x, y, z and Q are the same as above.

In the formulas (17) and (18), R'' is a group of the formula $-Si(R)_2-$, and more preferably of the formula $-Si(CH_3)_2-$, where R is the same as above.

Conditions for process 1 in regard to additional components in the reaction mixture, such as a platinum catalyst and a solvent, or the mixing ratios of the components and or the pressure and temperature apply as well to process 2.

In formula (16) above, x preferably has the value 2 or 3, and more preferably 2. Preferred cyclic siloxanes containing at least one alkenyl group of formula (16) bonded directly to silicon are thus cyclic siloxanes containing vinyl and/or allyl groups, and in particular those containing vinyl groups.

Cyclosiloxanes containing methyl and vinyl groups can be prepared, for example, by hydrolyzing dichlorosilane or cohydrolyzing this silane using dimethyldichlorosilane in a water/tetrahydrofuran mixture and subsequently subjecting the product to fractional distillation.

The preparation of 4-dimethylsilylchlorobenzene, the corresponding Grignard compound and 4-dimethylsilylbenzoic acid, prepared therefrom by reaction with $CO_2$, or the acid chloride is described in U.S. Pat. No. 4,914,221. The preparation involves reaction of 1,4-dichlorobenzene with magnesium to give 4-chloro benzenemagnesium chloride and reaction thereof with trichlorosilane.

Compounds of formulas (17) and (18) can be prepared from 4-dimethylsilyl-1-chlorobenzene analogously to that stated above for process 1 under the heading "Preparation of compounds of formulas (14) and (15):".

In all the processes described above, each compound present in the reaction mixture can be employed individually or as a mixture. Thus, for example, it is possible to employ in each case a reactant of one of the above mentioned formulas or a reactant which carries a radical of one of the above mentioned formulas, but it is also possible to employ a mixture of at least two such reactants. A solvent can be used if desired, and a catalyst can be used if necessary, but it is also possible to use a solvent mixture and/or a catalyst mixture.

The cyclic siloxanes of this invention or those that are capable of being prepared according to this invention and containing mesogenic side chains can be used in display devices, particularly in display devices produced using smectic liquid crystals or liquid crystal mixtures. These can use the pure compounds of this invention, mixtures thereof and in particular mixtures of the cyclic siloxanes of this invention with (other) liquid crystals. The compounds of this invention are suitable for the preparation of nematic, cholesteric and smectic mixtures, in particular mixtures which are able to form a smectic C phase. However, they can also be used as additives for nematic, smectic or cholesteric phases. With the aid of the cyclic siloxanes of this invention, the liquid-crystalline base mixtures can be prepared and the properties of base mixtures which have already been prepared, such as, for example, the optical anisotropy, the electrical anisotropy, the spontaneous polarization, the viscosity, the tilt angle, the pitch and the phase behavior, can be favorably modified.

The proportion of cyclic siloxanes of this invention containing mesogenic side groups in the liquid-crystal mixtures can be varied within broad limits depending on the application. For example, the proportion can be from 1 percent by weight up to 100 percent by weight.

In the table and examples below, unless otherwise specified, (a) all amounts are by weight;
(b) all pressures are 0.10 MPa (abs.); and
(c) all temperatures are at 20° C.

The phase descriptions are abbreviated as follows:
(d) the numbers denote transition temperatures, measured in °C.;
(e) the phase types are characterized as follows:
 I: isotropic phase,
 N: nematic phase,
 Chol: cholesteric phase,
 $S_A$: smectic A phase,
 $S_C$: smectic C phase
 $S_{C^*}$: chiral smectic C phase,
 $S_B$: smectic B phase,
 S: smectic state of undetermined type,
 C: crystalline,
 $T_G$: glass state.
(f) phase descriptions in parentheses indicate supercoolable phases.

TABLE 1

Starting materials of formula (14) or (15):
4-(ω-alkenyl)benzoic acid esters
cholesteryl 4-allylbenzoate C 139 Chol 203 I
cholesteryl 4-(3-butenyl)benzoate C 130 Chol 217
cholesteryl 4-(4-pentenyl)benzoate C 118 $S_A$ 125 Chol 194 I cholesteryl 4-(5-hexenyl)benzoate C 108 S$_A$ 128 Chol 197 I
4-methoxyphenyl 4-allylbenzoate C 85 I
4-methoxyphenyl 4-(3-butenyl)benzoate C 56 (N 40) I
4-methoxyphenyl 4-(4-pentenyl)benzoate C 49 I
4-methoxyphenyl 4-(5-hexenyl)benzoate C 59 I
4-cyanophenyl 4-allylbenzoate C 110 I
4-cyanophenyl 4-(3-butenyl)benzoate C 92 I
4-cyanophenyl 4-(4-pentenyl)benzoate C 44 I
4-cyanophenyl 4-(5-hexenyl)benzoate C 63 I
4-chlorophenyl 4-allylbenzoate C 54-56 I
4-chlorophenyl 4-(3-butenyl)benzoate C 50-51 I
4-chlorophenyl 4-(4-pentenyl)benzoate C 47 I
4-chlorophenyl 4-(5-hexenyl)benzoate C 54 I
4-biphenylyl 4-allylbenzoate C 146 I
4-biphenylyl 4-(3-butenyl)benzoate C 108 I
4-propylphenyl 4-(3-butenyl)benzoate C 24 I
4-biphenylyl 4-(4-pentenyl)benzoate C 127-128 I
4-biphenylyl 4-(5-hexenyl)benzoate C 114-118 I
4-octyloxyphenyl 4-(3-butenyl)benzoate C 42 N 61 I
4-cyanobiphenylyl 4-(3-butenyl)benzoate C 123 N 261 I
5-hexenyl 4-((4-chlorophenyl)carbonyloxyphenyl)benzoate C 52 I
5-hexenyl 4-((4-biphenylyl)carbonyloxyphenyl)benzoate C 98 I
4-trimethylsilybutylphenyl 4-(3-butenyl)benzoate b.p. 203°–204° C. at 0.2 mbar.

TABLE 2

Starting materials of the formula (14) or (15):
4-(ω-alkenyl)phenyl esters
4-(3-butenyl)phenyl 4-chlorobenzoate C 67 I
4-(3-butenyl)phenyl 4-biphenylycarboxylate C 97 N 107 I
4-(3-butenyl)phenyl 4-methoxybenzoate C 70 I
4-allylphenyl 4-biphenylylcarboxylate C 114 I
4-allylphenyl 4-methoxybenzoate C 63 I

TABLE 3

Cyclic siloxanes of this invention prepared by process 1
cyclopentasiloxane, pentamethyl-penta(4-cholesteryloxycarbonyl) phenylpropyl)- T$_G$ 82 S$_A$ 246 I
cyclopentasiloxane, pentamethyl-penta(4-cholesteryloxycarbonyl) phenylbutyl)-, T$_G$ 65 S$_A$ 240 I
cyclopentasiloxane, pentamethyl-penta(4-cholesteryloxycarbonyl) phenylpentyl)-, T$_G$ 51 S$_A$ 255 I
cyclopentasiloxane, pentamethyl-penta(4-cholesteryloxycarbonyl) phenylhexyl)-, T$_G$ 40 S$_A$ 248 I
cyclopentasiloxane, pentamethyl-penta(4-(4-methoxyphenyloxycarbonylphenyl)butyl)-, T$_G$ 10 N 5
cyclopentasiloxane, pentamethyl-penta(4-(4-cyanophenyloxycarbonylphenyl)propyl)-, T$_G$ 36 N 84 I
cyclopentasiloxane, pentamethyl-penta(4-(4-cyanophenyloxycarbonylphenyl)butyl)-, C 84 N 100 I
cyclopentasiloxane, pentamethyl-penta(4-(4-cyanophenyloxycarbonylphenyl)hexyl)-, C 54 S$_A$ 105 I
cyclopentasiloxane, pentamethyl-penta(4-(4-chlorophenyloxycarbonylphenyl)butyl)-, T$_G$ 50 S$_E$ 94 S$_A$ 115 I
cyclopentasiloxane, pentamethyl-penta(4-(4-chlorophenyloxycarbonylphenyl)hexyl)-. T$_G$ 2 S$_E$ 33 S$_A$ 120 I
cyclopentasiloxane, pentamethyl-penta(4-biphenylyloxycarbonylphenylbutyl)-, C 145 (T$_G$ 93 N 140) I
cyclopentasiloxane, pentamethyl-penta(4-biphenylyloxycarbonylphenylpentyl)-, C 120 N 142 I
cyclopentasiloxane, pentamethyl-penta(4-(4-biphenylylcarbonyloxy) phenylbutyl)-, T$_G$ 46 S$_x$ 117 S$_C$ 133 N 146 I
cyclopentasiloxane, pentamethyl-penta(4-(4-methoxyphenylcarbonyloxy)phenylbutyl)-, T$_G$ -3 N 65 I
cyclopentasiloxane, pentamethyl-penta(4-(4-biphenylylcarbonyloxy)phenylpropyl)-, T$_G$ 30 S$_B$ 57 S$_A$ 127 N 136 I
cyclopentasiloxane, pentamethyl-penta(4-(4-methoxyphenylcarbonyloxy)phenylpropyl)-, T$_G$ 7 N
cyclopentasiloxane, pentamethyl-penta(4-(4-cyanobiphenylyloxycarbonylphenyl)butyl)-, T$_G$ 48 S$_B$ 112 S$_A$ 144 N>300 I
cyclopentasiloxane, pentamethyl-penta(4-(4-cyanobiphenylyloxycarbonylphenyl)hexyl)-, T$_G$ 34 S$_B$ 112 S$_A$>300 I
cyclopentasiloxane, pentamethyl-penta(4-(4-chlorophenylcarbonyloxy)phenylcarbonyloxyhexyl)-, T$_G$ 5 S$_E$ 43 S$_B$ 83-90 S$_A$ 96-114 I
cyclopentasiloxane, pentamethyl-penta(4-(4-biphenylylcarbony loxy)phenylcarbonyloxyhexyl)-, T$_G$ 16 S$_A$, C 64 S$_A$ 176-192 I
cyclopentasiloxane, pentamethyl-(4-(cholesteryloxycarbonyl) phenyloxyhexyl)$_{1.25}$-[4-(biphenylyloxycarbonyl)phenyloxyhexyl]$_{1.25}$(4-(cholesteryloxycarbonyl)phenylbutyl)$_{1.25}$-(4-(biphenylyloxycarbonyl)phenylbutyl)$_{1.25}$. T$_G$ 41 S$_C$ 63-66 S$_A$ 173-177 Chol 201 I
cyclopentasiloxane, pentamethyl-(4-(cholesteryloxycarbonyl) phenylbutyl)$_{2.5}$-(4-(biphenylyloxycarbonyl)-phenylbutyl)$_{2.5}$ T$_G$ 44 S$_A$ 184 Chol 207 I
cyclopentasiloxane, pentamethyl-(4-(cholesteryloxycarbonyl) phenylpropyl)$_{2.5}$-(4-(4-methoxyphenyloxycarbonyl)-phenylbutyl)$_{2.5}$ T$_G$ 38 Chol 176 I
cyclopentasiloxane, pentamethyl-(4-(cholesteryloxycarbonyl) phenylbutyl$_{2.5}$-(4-(4-methoxyphenyloxycarbonyl)-phenylpropyl)$_{2.5}$ T$_G$ 37 Chol 170 I absorption maximum at 396 nm
cyclopentasiloxane, pentamethyl-(4-(cholesteryloxycarbonyl) phenylpropyl)$_3$-(4-(4-methoxyphenyloxycarbonyl)-phenylbutyl)$_2$ absorption maximum at 436 nm. T$_G$ 47 Chol 196 I
cyclopentasiloxane, pentamethyl-(4-(cholesteryloxycarbonyl) phenylpropyl)$_{1.75}$-(4(4-methoxyphenyloxycarbonyl)-phenylbutyl)$_{3.25}$ absorption maximum at 460 nm. T$_G$ 26 Chol 141 I
cyclopentasiloxane, pentamethyl-(4-(cholesteryloxycarbonyl) phenylpropyl)$_{0.75}$-(4-(4-methoxyphenyloxycarbonyl)phenylbutyl)$_{4.25}$ absorption maximum at 640 nm. T$_G$ 15 Chol 84 I
cyclotetrasiloxane, tetramethyl-(4-cholesteryloxycarbonyl) phenylpropyl)$_2$-(4-(4-methoxyphenyloxycarbonyl)-phenylbutyl)$_2$ T$_G$ 36 Chol 162-163 I absorption maximum at 460 nm
cyclohexasiloxane, hexa-[(4-butylphenyl)iminomethyl-4-phenylbutyl]hexamethyl C 75-103 i.

EXAMPLE 1

(a) Preparation of 4-(ω-alkenyl)-1-halobenzenes

A solution containing 294 g (2 mol) of 1,4-dichlorobenzene in 500 ml of anhydrous tetrahydrofuran was added dropwise over a period of about 110 minutes under nitrogen at 80° C. to a stirred suspension containing 48.6 g (2.0 mol) of magnesium turnings. The mixture was subsequently heated for 2 hours at 80°–84° C., then decanted from the excess magnesium, and the resultant solution of the Grignard compound was added dropwise over a period of 30 minutes at 80° C. to a stirred solution containing 194 g (1.8 mol) of 6-bromo-1-hexene (Fluka GmbH, 7910 Neu-Ulm) in 200 ml of tetrahydrofuran. The mixture was then stirred for 4 hours at 80° C. and then poured onto ice. After acidification with hydrochloric acid, the mixture was extracted three times with a 1:1 mixture of diethyl ether/methyl tert-butyl ether, and the ether fractions were stirred thoroughly with activated charcoal and dried over sodium sulfate. The filtrate was evaporated, and the residue was fractionated. At a pressure of 13 hPa and a temperature of 116°–118° C., 156 g (corresponding to a yield of 40% of theory) of 4-(5-hexenyl)-1-chlorobenzene were obtained. 4-(8-Nonenyl)-1-chlorobenzene (b.p. 87° C. at 0.3 hPa), for example, can also be prepared in the same way.

(b) Preparation of 4-($\omega$-alkenyl)benzoic acids

An initial amount of a total of 137 g (0.7 mol) of 4-(5-hexenyl)-1-chlorobenzene in 170 ml of tetrahydrofuran was added at 80° C. to 19.5 g (0.8 mol) of magnesium turnings. After the reaction had commenced, the remainder of the solution was added dropwise over a period of 2.5 hours with stirring at 80°–82° C., and the mixture was subsequently stirred for 4 hours at 80°–84° C.

About 150 ml of tetrahydrofuran were saturated at 10° C. with $CO_2$, and the Grignard solution decanted from the excess magnesium, was then added dropwise with stirring at 5°–15° C., and additional $CO_2$ was passed into the flask. When the addition was complete, a post-reaction time of 2 hours was allowed, and the mixture was poured onto ice and acidified using hydrochloric acid, and the resultant emulsion was extracted three times with methyl tert-butyl ether. Washing, drying and evaporation of the organic phase gave 73 g (47.6% of theory) of 4-(5-hexenyl)benzoic acid (recrystallization from petroleum ether gives a product having a melting range of 79°–82° C.).

Reaction of this acid with thionyl chloride in toluene using dimethylformamide as catalyst gave 65.6% of theory of the corresponding acid chloride (b.p. 118° C. at 13 mbar). Reaction of this acid chloride with 4-hydroxybiphenyl using triethylamine as acid scavenger gave a 61.8% yield of 4-biphenyl 4-(5-hexenyl)-benzoate, which has a melting range of 114°–118° C.

(c) Preparation of the cyclopentasiloxane adduct

About 5.7 g (15.3 mmol) of this ester, dissolved in 35 g of toluene, 0.9 g (0.3 mmol) of pentamethylcyclopentasiloxane (ABCR GmbH, 7500 Karlsruhe) and 0.8 ml of a 0.5% solution of dicyclopentadienylplatinum dichloride in dichloromethane were refluxed together for 60 minutes. The Pt catalyst was removed from the resultant solution by purification on a short silica gel column. The target product was precipitated using 200 ml of ethanol, filtered off and redissolved in pure toluene. Reprecipitation, filtration and drying gave 3.1 g (47% of theory) of pentamethyl-penta(4-biphenylyloxycarbonylphenylhexyl)cyclopentasiloxane, which has the following phase behavior: $S_I$ 117 $S_C$ 133 N 146–147 I.

EXAMPLE 2

Preparation of pentamethyl-penta-(4-(4-biphenylylcarbonyloxy)-phenylbutyl)cyclopentasiloxane (a) 4-Methoxymethoxy-1-bromobenzene was prepared from formaldehyde dimethyl acetal and 4-bromophenol by the method of Y. P. Yardley and H. Fletcher, Synthesis 1976, p. 244. The boiling point of this derivative is 54°–56° C. at 0.1 hPa, and the yield is 49% of theory.

About 4.6 g (0.19 mol) of magnesium turnings were moistened under nitrogen with absolute tetrahydrofuran, warmed to 60° C. and treated with a few drops of ethyl iodide as initiator. After the reaction had commenced, the remainder of a total of 35 g (0.16 mol) of the bromine compound, dissolved in 150 ml of tetrahydrofuran, was metered in at such a rate that the mixture continued to boil, and the mixture was subsequently refluxed for an additional 2.5 hours. A catalytic amount of a solution of dilithium tetrachlorocuprate (containing 25% of dilithium tetrabromocuprate) and a solution of 16.2 ml (0.16 mol) of 4-bromo-1-butene in 200 ml of THF were then added. The mixture was refluxed for 16 hours, then cooled and poured onto ice. After acidification and phase separation, the aqueous phase was extracted twice with 400 ml of methyl tert-butyl ether. The organic phases were dried and evaporated. The residue was fractionated under reduced pressure, giving 16.5 g (corresponding to 53.6% of theory) of 4-(methoxymethoxy)-1-(3-butenyl)benzene with a boiling point of 118°–120° C. and a pressure of 15 hPa.

Warming of this derivative at 95°–100° C. (40 hours) with 2N acetic acid liberated 20.8 g of 4-(3-butenyl)-phenol (42.1% of theory) at a pressure of 16 hPa and 130°–140° C.

(b) Esterification of this phenol derivative using commercial biphenyl-4-carbonyl chloride (Janssen Chimica, 4057 Brüggen 2) in toluene as solvent and with triethylamine as acid scavenger gave 4-(3-butenyl)phenyl-4-biphenylylcarboxylate in the form of colorless leaves in a yield of 76.2% of theory. The ester has the following phase behavior: C 97 N 107 I.

(c) The addition reaction of the resultant ester with pentamethylcyclopentasiloxane in accordance with the procedure of Example 1 (c) gave the desired product in a virtually quantitative yield. The following phases were observed: $T_G$ 46 $S_x$ 125 $S_B$ 137 $S_A$ 170 I.

EXAMPLE 3

Preparation of tetramethyl-di(4-(cholesteryloxycarbonyl)-phenylpropyl)-di(4-(4-methoxyphenyloxycarbonyl)phenylbutyl)cyclotetrasiloxane About 4-Methoxyphenyl 4-(3-butenyl)benzoate (m.p. 54° C.) and cholesteryl 4-allylbenzoate (C 139 Chol 203 I) were prepared analogously to Examples 1(a) and (b) respectively, and added in equimolar amounts, as described in Example 1(c), to tetramethylcyclotetrasiloxane. After purification, the resultant product had the following behavior: glass transition temperature ($T_G$) 36 Chol 162–163 I. The absorption spectrum had a maximum at 460 nm.

EXAMPLE 4

Preparation of hexa[(4-butylphenyl)iminomethyl-4-phenylbutyl]hexamethylcyclohexasiloxane (a) First, 4-(3-butenyl)-1-bromobenzene was prepared by the method of P. E. Peterson et al., J. Org. Chem. 33, 972 (1968). About 133 g (0.63 mol) of this product were dissolved in 110 ml of tetrahydrofuran, and the mixture was added dropwise over a period of about 3 hours at 75°-95° C. with stirring to 17 g (0.7 mol) of magnesium turnings. The mixture was then cooled, the Grignard solution was decanted off from the magnesium and added dropwise over a period of about 2 hours at 5°-10° C. to a solution containing 57.7 g (0.8 mol) of dimethylformamide in 35° C. for an additional hour. After the mixture had been cooled, hydrolyzed and worked up, the organic phase was fractionated in a short column, giving 56.2 g of 4-(3-butenyl)benzaldehyde (55.7% yield) at a pressure of 16 mbar and a boiling point of 124° C.

(b) About 26.0 g (0.1 mol) of this aldehyde and 14.9 g (0.1 mol) of commercially available 4-butylaniline were dissolved in 200 ml of toluene, 0.3 g of 4-toluenesulfonic acid was added as catalyst, and the mixture was refluxed for 90 minutes. The water formed was removed azeotropically via a separator. The reaction residue was fractionated. The desired imine had a boiling point of 170° C. at 0.02 mbar. About 19.1 g of substance (65.6% of theory) were obtained after recrystallization from ethanol.

(c) About 1.6 g (4.5 mmol) of hexamethylcyclohexasiloxane and 8.7 g (30 mmol) of the imine from (b) were reacted (60 minutes) analogously to Example 1(c) at 50°-90° C. in 10 ml of toluene with the aid of 0.4 ml of a 0.5% platinum catalyst solution. Reprecipitation twice from ethanol gave 6.5 g (68% of theory) of the desired adduct, which has the following phase behavior: C, 56 $S_A$ 88–103 I.

EXAMPLE 5

Comparison Example

About 4-propylphenyl 4-allyloxybenzoate (melting point 53°-55° C.) and 4-propylphenyl 4-(3-butenyl)benzoate (melting point 24° C.) were reacted under identical reaction conditions with the pentamethylcyclopentasiloxane described in Example 1(c). In the case of both substances, the solvent was first removed and $^1$H-NMR spectra were recorded for the unpurified residues.

The adduct of 4-(3-butenyl)benzoate exhibits the expected signals with clear resolution; the integrals of the individual signals correspond to one another.

The adduct of 4-allylbenzoate exhibits individual signals with multiple splitting (caused by by-products). The heights of the integrals of the individual signals differ from one another by up to 20%. A comparison of the high-pressure gel permeation chromatograms shows that the 4-allyloxybenzoate adduct contains more than twice the contamination caused by by-products as the 4-(3-butenyl)benzoate adduct (no oxygen in the spacer).

Both crude products were dissolved in toluene and purified by chromatography in equal length columns containing silica gel. This showed the 4-(3-butenyl)benzoate adduct to contain 3.2% of impurities, while, by contrast, the 4-allyloxybenzoate adduct contained 28.7% of impurities. The increased proportion of impurities compared with the crude product is caused by the silica gel used for chromatography, whose surface water is sufficient, in spite of the aprotic eluent, to cause considerably hydrolysis.

EXAMPLE 6

Comparison Example

A 1:1 mixed adduct, prepared as described in EP 60 335, of cholesteryl 4-(propen-2-oxy)benzoate and 4'-phenylphenyl 4-(propen-2-oxy)phenylbenzoate with pentamethylcyclopentasiloxane has a broad absorption region (52 nm) at 632-580 nm whose broadening is caused by by-products. A comparable 1:1 adduct according to the invention of cholesteryl 4-(3-butenyl)benzoate and 4-methoxyphenyl 4-(2-propen-1-yl)benzoate with pentamethylcyclopentasiloxane has a significantly narrower absorption region (25 nm) at 380–405 nm.

EXAMPLE 7

Preparation by Process 2

About 0.65 g (1.89 mmol) of 1,2,3,4-tetravinyl-1,2,3,4-tetramethylcyclotetrasiloxane, 2.50 g (7.53 mmol) of 4-biphenyl 4-dimethylsilylbenzoate and 80 mg (2 μmol of Pt) of 1% dicyclopentadienylplatinum dichloride solution in dichloromethane were refluxed for 30 minutes in 5 ml of dry toluene. The reaction product was precipitated from the toluene using methanol and purified by chromatography on silica gel, giving a 78% yield of 1,2,3,4-tetrakis(2-(4-biphenyloxycarbonylphenylene-4-dimethylsilylene)ethyl)-1,2,3,4-tetramethylcyclotetrasiloxane, phases: C 82–85 i.

The following were prepared analogously:

1,2,3-tris(2-(cholesteryloxycarbonylphenylene-4-dimethylsilylene) ethyl)-1,2,3-trimethylcyclotrisiloxane, phases: G 63 $S_C$ 141–157 i;1,2,3,4-tetrakis(2-(cholesteryloxycarbonylphenylene-4-dimethylsilylene)ethyl)-1,2,3,4-tetramethylcyclotetrasiloxane, phases: $T_G$ 67 $S_C$ 164 I;

1,2,3-tris(2-(4-biphenyloxycarbonylphenylene-4-dimethylsilylene) ethyl)-1,2,3-trimethylcyclotrisiloxane, phases: C 88 (G 46) I;

1-(2-(cholesteryloxycarbonylphenylene-4-dimethylsilylene)ethyl) -2,3-bis(2-(4-biphenyloxycarbonylphenylene-4-dimethylsilylene) ethyl)-1,2,3-trimethylcyclotrisiloxane, phases: $T_G$ 41 $s_c$ 86 I;

1,2-bis(2-(cholesteryloxycarbonylphenylene-4-dimethylsilylene) ethyl)-3-(2-(4-biphenyloxycarbonylphenylene-4-dimethylsilylene) ethyl)-1,2,3-trimethylcyclotrisiloxane, phases: $T_G$ 47 $s_c$ 126 I;

1,2,3,4,5-pentakis(2-(cholesteryloxycarbonylphenylene-4-dimethylsilylene)ethyl)-1,2,3,4,5-pentamethylcyclopentasiloxane, phases: $T_G$ 80 $s_c$ 179–196 I;

1,2,3-tris(2-(cholesteryloxycarbonylphenylene-4-dimethylsilylene) ethyl)-4-(2-(4-biphenyloxycarbonylphenylene-4-dimethylsilylene) ethyl)-1,2,3,4-etramethylcyclotetrasiloxane, phases: $T_G$ 61 $s_4$ 146–153 I;

1,2-bis(2-(cholesteryloxycarbonylphenylene-4-dimethylsilylene) ethyl(-3,4-bis(2-(4-biphenyloxycarbonylphenylene-4-dimethylsilylene)ethyl-1,2,3,4-tetramethylcyclotetrasiloxane, phases: $T_G$ 50 s 105–120 I;

1-(2-cholesteryloxycarbonylphenylene-4-dimethylsilylene)-ethyl) -2,3,4-tris(2-(4-biphenyloxycarbonylphenylene-4-dimethylsilylene) ethyl-1,2,3,4-tetramethylcyclotetrasiloxane, phases: $T_G$ 39 s 84–88 I;

1,2-bis(2-(cholesteryloxycarbonylphenylene-4-dimethylsilylene) ethyl)-3,4-bis(2-(4-methoxyphenyloxycarbonylphenylene -4-dimethylsilylene)ethyl)-1,2,3,4-tetramethylcyclotetrasiloxane, phases: $T_G$ 40 s 58 I;

1,2,3,4-tetrakis(2-(4-cyanophenyleneoxycarbonylphenylene-4-dimethylsilylene)ethyl)-1,2,3,4-tetramethylcyclotetrasiloxane, phases: $T_G$ 37 I;

1,2,3,4-tetrakis[2-(4,4'-cyanobiphenylyloxycarbonylphenylene-4-dimethylsilylene)ethyl]-1,2,3,4-tetramethylcyclotetrasiloxane; phases: $T_G$ 52 $s_c$ 214 $s_A$214-228 I.

What is claimed is:

1. A cyclic siloxane which has at least one group of formula (1) bonded to a silicon atom

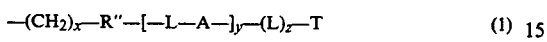
—(CH$_2$)$_x$—R''—[—L—A—]$_y$—(L)$_z$—T   (1)

in which x is an integer having a value of from 2 to 10, R'' is selected from the group consisting of a chemical bond, and a divalent radical selected from the group consisting of the formulas —COO—, —OOC—, —CH$_2$—CH$_2$, —CH=CH—, —C≡C—, —CH=N—, —N=CH— and —Si(R)$_2$—, where the radical R is selected from the group consisting of a hydrocarbon radical having from 1 to 18 carbon atoms and a substituted hydrocarbon radical having from 1 to 18 carbon atoms, L is selected from the group consisting of the 1,4-phenylene and the 1,4-cyclohexylene radicals which are optionally substituted at the 2-, 3-, 5- and/or 6-position by radical Q, Q is selected from the group consisting of hydrogen, fluorine, chlorine, cyano, methyl and trifluoromethyl groups, A is a radical selected from the group consisting of the divalent radicals R'', or of the formula —CH$_2$—O— and —O—CH$_2$—, y is an integer having a value of from 0 to 10, z is an integer having a value of from 0 to 10, with the proviso that the sum y+z is at least 1, and T is selected from the group consisting of a hydrocarbon radical having from 1 to 18 carbon atoms and a substituted hydrocarbon radical having from 1 to 18 carbon atoms, in which the substituents are selected from the group consisting of halogen atoms, cyano groups, nitro groups, hydrocarbonoxy groups having 1 to 10 carbon atoms and mixtures thereof.

2. A cyclic siloxane which has at least one group of formula (2) bonded to a silicon atom

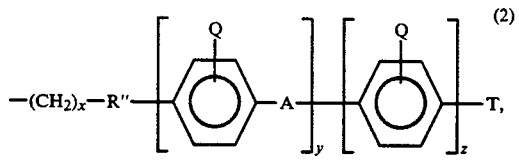
(2)

in which x is an integer having a value of from 2 to 10, R'' is selected from the group consisting of a chemical bond, and a divalent radical selected from the group consisting of the formulas —COO—, —OOC—, —CH$_2$—CH$_2$—, —CH=CH—, —C≡C—, —CH=N—, —N=CH— and —Si(R)$_2$—, where the radical R is selected from the group consisting of a hydrocarbon radical having from 1 to 18 carbon atoms and a substituted hydrocarbon radical having from 1 to 18 carbon atoms, Q is selected from the group consisting of hydrogen, fluorine, chlorine, cyano, methyl and trifluoromethyl groups, A is a radical selected from the group consisting of the divalent radicals R'', —CH$_2$—O—, and —O—CH$_2$—, y is an integer having a value of from 0 to 10, z is an integer having a value of from 0 to 10, with the proviso that the sum y+z is at least 1, and T is selected from the group consisting of a hydrocarbon radical having from 1 to 18 carbon atoms and a substituted hydrocarbon radical having from 1 to 18 carbon atoms, in which the substituents are selected from the group consisting of halogen atoms, cyano groups, nitro groups, hydrocarbonoxy groups having 1 to 10 carbon atoms and mixtures thereof.

3. An organocyclosiloxane of the formula

[RXSiO]$_n$   (5)

in which at least one X is selected from the group consisting of (a) a radical of the formula

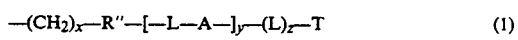
—(CH$_2$)$_x$—R''—[—L—A—]$_y$—(L)$_z$—T   (1)

and (b) a radical of the formula

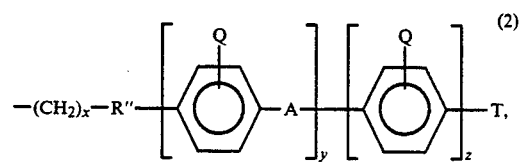
(2)

where the radical R is selected from the group consisting of a hydrocarbon radical having from 1 to 18 carbon atoms and a substituted hydrocarbon radical having from 1 to 18 carbon atoms, and the remaining X radicals are the same as R, R'' is selected from the group consisting of a chemical bond, and a divalent radical selected from the group consisting of the formulas —COO—, —OOC—, —CH$_2$—CH$_2$, —CH=CH—, —C≡C—, —CH=N—, —N=CH— and —Si(R)$_2$—, L is selected from the group consisting of the 1,4-phenylene and the 1,4-cyclohexylene radicals which are optionally substituted at the 2-, 3-, 5- and/or 6 position by radical Q, Q is selected from the group consisting of hydrogen, fluorine, chlorine, cyano, methyl and trifluoromethyl groups, A is a radical selected from the group consisting of the divalent radicals R'' or of the formula —CH$_2$—O— and —O—CH$_2$—, y is an integer having a value of from 0 to 10, z is an integer having a value of from 0 to 10, with the proviso that the sum y+z is at least 1, and T is selected from the group consisting of a hydrocarbon radical having from 1 to 18 carbon atoms, and a substituted hydrocarbon radical having from 1 to 18 carbon atoms, in which the substituents are selected from the group consisting of halogen atoms, cyano groups, nitro groups, hydrocarbonoxy groups having 1 to 10 carbon atoms and mixtures thereof, x is an integer having a value of from 2 to 10, and with a further proviso that the q radicals X per molecule of formula (5) are radicals of formula (1), and the radical R'' has been replaced in the maximum of q-1 of these radicals of formula (1) by a radical selected from the group consisting of the formulas —O—, —CH$_2$—O— and —O—CH$_2$—, q is an integer having a value of from 1 to n, and n is an integer having a value of at least 3.

4. A cyclic siloxane which has at least one group of formula (1) bonded to a silicon atom

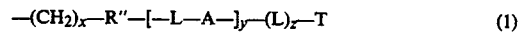
—(CH$_2$)$_x$—R''—[—L—A—]$_y$—(L)$_z$—T   (1)

in which x is an integer having a value of from 2 to 10, R'' is selected from the group consisting of a chemical bond, and a divalent radical selected from the group consisting of the formulas —COO—, —OOC—, —CH$_2$—CH$_2$, —CH=CH—, —C≡C—, —CH=N—, —N=CH— and —Si(R)$_2$—, where the radical R is selected from the group consisting of a hydrocarbon radical having from 1 to 18 carbon atoms and a substituted hydrocarbon radical having from 1 to 18 carbon atoms, L is selected from the group consisting of the group consisting of the 1,4-phenylene and the 1,4-cyclohexylene radicals which are optionally substituted at the 2-, 3-, 5- and/or 6 position by radical Q, Q is selected from the group consisting of hydrogen, fluorine, chlorine, cyano, methyl and trifluoromethyl groups, A is a radical selected from the group consisting of the divalent radicals R″ or of the formula —CH$_2$—O—, and —O—CH$_2$—, y is an integer having a value of from 0 to 10, z is an integer having a value of from 0 to 10, with the proviso that the sum y+z is at least 1, and T is selected from the group consisting of a hydrocarbon radical having from 1 to 18 carbon atoms, and a substituted hydrocarbon radical having from 1 to 18 carbon atoms, in which the substituents are selected from the group consisting of halogen atoms, cyano groups, nitro groups, hydrocarbonoxy groups having 1 to 10 carbon atoms and mixtures thereof, in which the cyclosiloxane of formula (1) is obtained by reacting a cyclic siloxane having at least one hydrogen atom bonded directly to silicon with a compound selected from the group consisting of formulas

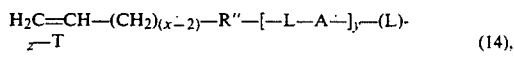
(14), and

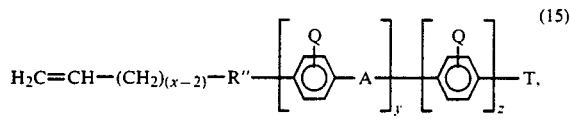
(15)

in which R″, L, Q, A, T, y, x and z are the same as above.

5. A process for preparing the cyclosiloxane of claim 3, which comprises reacting a cyclic siloxane having at least one alkenyl group of the formula

(16), bonded directly to silicon with a compound selected from the group consisting of the formulas

(17)

and

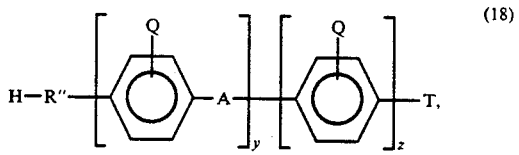
(18)

in which R″ is —Si(R)$_2$—, where the radical R is selected from the group consisting of a hydrocarbon radical having from 1 to 18 carbon atoms and a substituted hydrocarbon radical having from 1 to 18 carbon atoms, L is selected from the group consisting of the 1,4-phenylene and the 1,4-cyclohexylene radicals which are optionally substituted at the 2-, 3-, 5- and/or 6 position by radical Q, Q is selected from the group consisting of hydrogen, fluorine, chlorine, cyano, methyl and trifluoromethyl groups, A is a radical selected from the group consisting of a chemical bond, and a divalent radical selected from the group consisting of the formulas —COO—, —OOC—, —CH$_2$—CH$_2$—, —CH=CH—, —C≡C—, —CH=N—, —N=CH—, —Si(R)$_2$—, —CH$_2$—O— and —O—CH$_2$—, y is an integer having a value of from 0 to 10, z is an integer having a value of from 0 to 10, with the proviso that the sum y+z is at least 1, and T is selected from the group consisting of a hydrocarbon radical having from 1 to 18 carbon atoms and a substituted hydrocarbon radical having from 1 to 18 carbon atoms, in which the substituents are selected from the group consisting of halogen atoms, cyano groups, nitro groups, hydrocarbonoxy groups having 1 to 10 carbon atoms and mixtures thereof, x is an integer having a value of at least 2.

* * * * *